US010918656B2

(12) United States Patent
Oshita et al.

(10) Patent No.: US 10,918,656 B2
(45) Date of Patent: *Feb. 16, 2021

(54) THERAPEUTIC AGENT FOR DRY EYE CHARACTERIZED BY BEING APPLIED TO EYE OF DRY EYE PATIENT WEARING SOFT CONTACT LENS

(71) Applicant: SANTEN PHARMACEUTICAL CO., LTD., Osaka (JP)

(72) Inventors: Yoshihiro Oshita, Osaka (JP); Hitoshi Nakazawa, Ikoma (JP); Isao Matsuoka, Ikoma (JP); Asuka Kamimura, Ikoma (JP)

(73) Assignee: SANTEN PHARMACEUTICAL CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/862,662

(22) Filed: Apr. 30, 2020

(65) Prior Publication Data
US 2020/0254000 A1    Aug. 13, 2020

Related U.S. Application Data

(63) Continuation of application No. 15/579,481, filed as application No. PCT/JP2016/066590 on Jun. 3, 2016.

(30) Foreign Application Priority Data

Jun. 5, 2015 (JP) ................................ 2015-114596

(51) Int. Cl.
*A61K 31/7084* (2006.01)
*A61P 27/04* (2006.01)
*A61K 9/00* (2006.01)
*A61K 47/10* (2017.01)
*A61K 47/14* (2017.01)

(52) U.S. Cl.
CPC ........ *A61K 31/7084* (2013.01); *A61K 9/0048* (2013.01); *A61K 47/10* (2013.01); *A61K 47/14* (2013.01); *A61P 27/04* (2018.01)

(58) Field of Classification Search
None
See application file for complete search history.

(56) References Cited

U.S. PATENT DOCUMENTS

| 4,029,817 | A  | 6/1977  | Blanco et al.     |
| 6,153,607 | A  | 11/2000 | Pflugfelder et al.|
| 6,180,093 | B1 | 1/2001  | De et al.         |
| 6,703,376 | B2 | 3/2004  | Jacobus et al.    |
| 9,107,888 | B2 | 8/2015  | Nishihata et al.  |
| 9,561,280 | B2 | 2/2017  | Nishihata et al.  |
| 2002/0103157 | A1 | 8/2002  | Yerxa et al.      |
| 2004/0214754 | A1 | 10/2004 | Ellis et al.      |
| 2010/0130580 | A1 | 5/2010  | Ousler et al.     |
| 2012/0108672 | A1 | 5/2012  | Tsutsui et al.    |
| 2013/0172287 | A1 | 7/2013  | Shichijo et al.   |
| 2013/0281537 | A1 | 10/2013 | Nishihata et al.  |
| 2014/0221306 | A1 | 8/2014  | Sakatani et al.   |
| 2015/0072951 | A1 | 3/2015  | Sakatani et al.   |
| 2015/0306222 | A1 | 10/2015 | Nishihata et al.  |

FOREIGN PATENT DOCUMENTS

| JP | 2001-501605 A    | 2/2001  |
| JP | 3652707 B2       | 5/2005  |
| JP | 2011-026303 A    | 2/2011  |
| JP | 2012-149057 A    | 8/2012  |
| JP | 2013-227291 A    | 11/2013 |
| KR | 10-2014-0012061 A| 1/2014  |
| WO | 2012/016000 A2   | 2/2012  |
| WO | 2016/104704 A1   | 6/2016  |

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
International Search Report (PCT/ISA/210) dated Aug. 30, 2016, by the Japanese Patent Office as the International Searching Authority for International Application No. PCT/JP2016/066590.
Written Opinion (PCT/ISA/237) dated Aug. 30, 2016, by the Japanese Patent Office as the International Searching Authority for International Application No. PCT/JP2016/066590.
J. Ogawa, Q&A de Wakaru Allergy Shikkan, 2007, vol. 3, No. 2, pp. 138-139.
N. L.Burstein, The effects of topical drugs and preservatives on the tears and corneal epithelium in dry eye, Transactions of the ophthalmological societies of the United Kingdom, 1985, vol. 104, Pt. 4, p. 402-409.
A.J. Duncan et al., Some preservatives in eyedrop preparations hasten the formation of dryspots in the rabbit cornea, British Journal of Pharmacology, 1976, vol. 56, No. 3, 359P-360P.
Search Report submitted to the Korean Patent Office by WIPS (A Korean Prior Art Search Organization) on May 19, 2018, in corresponding Korean Patent Application No. 10-2017-7037651 (8 pages).
Dogru et al.: "Changing trends in the treatment of dry-eye disease," Expert Opinion on Investigational Drugs, 2013, vol. 22, No. 12, pp. 1581-1601 (22 pages).
Takamura et al.: "A randomised, double-masked comparison study of diquafosol versus sodium hyaluronate ophthalmic solutions in dry eye patients," Br J Ophthalmol, 2012;96: 1310-1315 (6 pages).
Keating: "Diquafosol Ophthalmic Solution 3 %: A Review of Its Use in Dry Eye," Drugs, 2015, vol. 75, No. 8, pp. 911-922, (First Online: May 13, 2015).
Nixon: "Contact Lens Practice Pearls—Maintaining Lens Hydration," Contact Lens Spectrum, May 1, 2012, vol. 27, pp. 42.
Notice of Submission of Publications, etc. in corresponding Japanese Patent Application No. 2016-111472, mailed by the Japanese Patent Office to applicant on Aug. 6, 2019 (3 pages including partial English translation).
Submission of Publication, etc. submitted to the Japanese Patent Office in corresponding Japanese Patent Application No. 2016-111472 on Jul. 8, 2019 (15 pages including partial English translation).

(Continued)

*Primary Examiner* — Dale R Miller
(74) *Attorney, Agent, or Firm* — Buchanan, Ingersoll & Rooney PC

(57) ABSTRACT

An ophthalmic solution, which comprises diquafosol tetrasodium salt and is free from benzalkonium chloride, treats onset and/or exacerbation of dry eye symptom caused by wearing soft contact lenses.

4 Claims, 1 Drawing Sheet

(56) References Cited

OTHER PUBLICATIONS

Diquas ophthalmic solution 3% Package Insert, Publication date: Jan. 2014 (4 pages including partial English translation).
Hyalein ophthalmic solution Package Insert, Publication date: Oct. 2009 (6 pages including partial English translation).
Ophthalmology, vol. 56, No. 3, pp. 355-361, Publication date: Feb. 2014 (8 pages including partial English translation).
"Effects of Ophthalmic Preservative on the Corneal Epithelium," Journal of the Eye, vol. 8, No. 10, pp. 1599-1603, Publication date: Oct. 1991 (3 pages including English abstract).
Ohashi et al.: Contact lens Ad libitum, pp. 120-123, Publication date: Jun. 2004 (4 pages including partial English translation).
Ueda: "Adsorption and Release of Preservative from Soft Contact Lenses," Journal of Japan Contact Lens Society, vol. 49, No. 3, pp. 182-186, Publication date: Mar. 2007 (4 pages including English abstract).
EMEA: "EMEA Public Statement on Antimicrobial Preservatives in Ophthalmic Preparations for Human Use," European Medicines Agency, Publication date: Dec. 2009 (1 page).
Sodium Hyaluronate ophthalmic solution "TS" Package Insert, Publication date: Sep. 2018, Sales commenced: Nov. 2011 (3 pages including partial English translation).
Yokoi: Frontiers in Dry eye, vol. 7, No. 2, pp. 50-55, Publication date: Oct. 2012 (7 pages including partial English translation).
Ishibashi et al.: "Comparison of the Short-Term Effects on the Human Corneal Surface of Topical Timolol Maleate With and Without Benzalkonium Chloride," J Glaucoma, vol. 12, No. 6, pp. 486-490, Publication date: Dec. 2003 (5 pages).
Notice of Submission of Publications, etc. in corresponding Japanese Patent Application No. 2016-111472, mailed by the Japanese Patent Office to applicant on Aug. 13, 2019 (3 pages including partial English translation).
Submission of Publication, etc. submitted to the Japanese Patent Office in corresponding Japanese Patent Application No. 2016-111472 on Jul. 19, 2019 (17 pages including partial English translation).
"Explanation of 'Precautions for use' of new drugs," of Mucosta ophthalmic suspension UD2%, pp. 1-12, Jul. 2012 Revised 3rd edition (14 pages including partial English translation).
Santen Pharmaceutical Co., Ltd. "News Release: 'Fatigue of eyes' comes with contact lenses . . . !? 'Soft Santear Hitomi Stretch', a drug for eye fatigue (compatible with contact lenses) which relieves the focus adjustment muscle stiffness that causes fatigue of eyes, launched," Sep. 9, 2014 (3 pages including partial English translation).
Wakamoto Pharmaceutical Co., Ltd., Nipro Corporation "Production of a new eye drop container that enables preservative free," announced on May 30, 2007 (2 pages including partial English translation).
Saji et al.: "Studies of Antibacterial Activity of Benzalkonium Chloride as Preservative for Ophthalmic Solutions Against Gram-positive Cocci and Negative Rods," Jpn. J. Pharm. Health Care Sci., 2003, vol. 29, No. 3, pp. 341-345 (6 pages including partial English translation).
Office Action issued by the Russian Patent Office in corresponding Russian Patent Application No. 2017145545 dated Nov. 20, 2019 (11 pages including partial English translation).
"Dry eye syndrome—Don't drop too much artificial tears," Sep. 23, 2014, 12:40 United Daily News, Taiwan Shin Sheng Daily News, (5 pages including partial English translation).
Office Action issued by the Taiwanese Patent Office in corresponding Taiwanese Patent Application No. 105117569 dated Feb. 27, 2020 (6 pages).

* cited by examiner

THERAPEUTIC AGENT FOR DRY EYE CHARACTERIZED BY BEING APPLIED TO EYE OF DRY EYE PATIENT WEARING SOFT CONTACT LENS

CROSS-REFERENCE TO RELATED APPLICATIONS

This application is a continuation of U.S. application Ser. No. 16/579,481, filed Dec. 4, 2017, now U.S. Pat. No. 10,729,712, which is a U.S. national stage application of PCT/JP2016/066590, filed Jun. 3, 2016, which claims priority to Japanese Patent Application No. 2015-114596, filed Jun. 5, 2015, the entire contents of all of which are hereby incorporated by reference.

TECHNICAL FIELD

The present invention relates to a therapeutic agent for dry eye characterized by being applied to an eye of a dry eye patient wearing soft contact lens, which comprises diquafosol or a salt thereof as an active ingredient and does not comprise benzalkonium chloride.

BACKGROUND ART

Although dry eye is a disease that initially exhibits merely unpleasant symptoms such as dryness of the eyes or eyes that feel sandy or gritty, as the condition worsens, it causes considerable difficulties during the course of daily life. The number of the dry eye patients is increasing year by year with advent of an aging society and the increase in video display terminal (VDT) work such as personal computers, the estimated number of patients in the United States is over 10 million people, and in Japan, it is said to be more than 8 million people.

Although the pathology of dry eye is not completely clear, it is thought that the main cause is the decrease of lacrimal secretion and the increase of lacrimal evaporation accompanied by the decrease of the stability of the tear film. That is, these cause pathological symptom and/or findings such as eye discomfort, eye dryness, eye fatigue, hyperemia, keratoconjunctival epithelial disorders and the like. If these pathological symptoms and/or findings progress, vision abnormalities are ultimately generated, so that it is extremely important to treat the dry eye at an early stage and properly.

Wearing a soft contact lens leads to decrease in the stability of the tear film, so wearing soft contact lenses for dry eye patients may lead to exacerbation of dry eye symptoms. In addition, dry eye also may develop by wearing soft contact lenses. However, even with such a dry eye patient, there are cases where it is not desired to stop wearing soft contact lenses from the viewpoint of convenience.

On the other hand, in Japan, there are no widely recognized pharmaceuticals for treating onset and/or exacerbation of dry eye symptom caused by wearing soft contact lenses. Rather, in Japan, with regard to "DIQUAS® ophthalmic solution 3%", "Hyalein® ophthalmic solution 0.1%" and "Hyalein® ophthalmic solution 0.3%" which have widely been used for dry eye patients, the use themselves for soft contact lens wearers is contraindicated.

By the way, the above-mentioned "DIQUAS® ophthalmic solution 3%" contains diquafosol tetrasodium salt at a concentration of 3% (w/v) as an active ingredient, and further contains benzalkonium chloride as a preservative. Diquafosol is a purinergic receptor agonist also called as $P^1,P^4$-di(uridine-5') tetraphosphate or $Up_4U$, and it has been known to have a lacrimation-promoting function as disclosed in Patent Document 1. However, it has not been known what effect diquafosol has on the onset and/or exacerbation of dry eye symptom caused by wearing soft contact lenses.

PRIOR ART DOCUMENTS

Patent Documents

Patent Document 1: Japanese Patent No. 3652707

DISCLOSURE OF THE INVENTION

Problems to be Solved by the Invention

Accordingly, it is an interesting problem to search for pharmaceuticals to treat onset and/or exacerbation of dry eye symptom caused by wearing soft contact lenses.

Means for Solving the Problems

The present inventors have intensively studied to search pharmaceuticals which can treat onset and/or exacerbation of dry eye symptom caused by wearing soft contact lenses, and as a result, they have found that when eyes wearing soft contact lenses of cynomolgus monkeys are treated with an ophthalmic solution which contains diquafosol tetrasodium salt and does not contain benzalkonium chloride (hereinafter also referred to as "present ophthalmic solution"), significant increase in non-invasive break up time (NIBUT) which could not be recognized in an artificial tear solution, i.e., stabilization of the tear film, whereby the present invention has accomplished. As described in the section on the background art, since the onset and/or exacerbation of dry eye symptoms caused by wearing soft contact lenses is attributable to decrease in the stability of the tear film, so that stabilization of the tear film contributes to the treatment of dry eye of soft contact lens wearers.

That is, the present invention is to provide a therapeutic agent for dry eye mentioned below.

(1) A therapeutic agent for dry eye characterized by being applied to an eye of a dry eye patient wearing soft contact lens, which comprises diquafosol or a salt thereof as an active ingredient and does not comprise benzalkonium chloride (hereinafter also referred to as "the present agent").
(2) The therapeutic agent described in (1), which is contained in a unit-dose type.
(3) The therapeutic agent described in (1), which is contained in a multi-dose type.
(4) The therapeutic agent described in (3), which comprises a preservative other than benzalkonium chloride.
(5) The therapeutic agent described in (4), wherein the preservative other than benzalkonium chloride is at least one selected from the group consisting of chlorhexidines, borates, chlorites, parabenes, sorbates, chlorobutanol and benzethonium chloride.
(6) The therapeutic agent described in (4) or (5), wherein the preservative other than the benzalkonium chloride is chlorhexidines.
(7) The therapeutic agent described in any one of (1) to (6), wherein the concentration of the diquafosol or a salt thereof is 0.5 to 5% (w/v).
(8) The therapeutic agent described in any one of (1) to (7), wherein the concentration of the diquafosol or a salt thereof is 3% (w/v).

(9) The therapeutic agent described in (1), wherein the dry eye is caused by wearing contact lens.

In addition, the present invention provides an ophthalmic solution mentioned below.

(10) An ophthalmic solution for improving tear film stability, characterized by being applied to an eye wearing soft contact lens, which comprises diquafosol or a salt thereof as an active ingredient and does not comprise benzalkonium chloride.

(11) An ophthalmic solution for treating eye dryness or eye discomfort caused by wearing soft contact lens, characterized by being applied to an eye wearing soft contact lens, which comprises diquafosol or a salt thereof as an active ingredient and does not comprise benzalkonium chloride.

The present invention also relates to the following.

(12) An ophthalmic solution for use in treatment of dry eye, which comprises diquafosol or a salt thereof as an active ingredient and does not comprise benzalkonium chloride, wherein the ophthalmic solution is applied to an eye of a dry eye patient wearing soft contact lens.

(13) An ophthalmic solution for use in improvement of tear film stability, which comprises diquafosol or a salt thereof as an active ingredient and does not comprise benzalkonium chloride, wherein the ophthalmic solution is applied to an eye wearing soft contact lens.

(14) An ophthalmic solution for use in treatment of eye dryness or eye discomfort caused by wearing soft contact lens, which comprises diquafosol or a salt thereof as an active ingredient and does not comprise benzalkonium chloride, wherein the ophthalmic solution is applied to an eye wearing soft contact lens.

Further, the present invention relates to the following.

(15) Use of an ophthalmic solution which comprises diquafosol or a salt thereof as an active ingredient and does not comprise benzalkonium chloride, for the manufacture of a medicine for treating dry eye, characterized by being applied to an eye of a dry eye patient wearing soft contact lens.

(16) Use of an ophthalmic solution which comprises diquafosol or a salt thereof as an active ingredient and does not comprise benzalkonium chloride, for the manufacture of a medicine for improving tear film stability, characterized by being applied to an eye wearing soft contact lens.

(17) Use of an ophthalmic solution which comprises diquafosol or a salt thereof as an active ingredient and does not comprise benzalkonium chloride, for the manufacture of a medicine for treating eye dryness or eye discomfort caused by wearing soft contact lens, characterized by being applied to an eye wearing soft contact lens.

Moreover, the present invention relates to the following.

(18) A method of treating dry eye, which comprises administering an ophthalmic solution which comprises a therapeutically effective amount of diquafosol or a salt thereof and does not comprise benzalkonium chloride to an eye of a dry eye patient wearing soft contact lens.

(19) A method of improving tear film stability, which comprises administering an ophthalmic solution which comprises a therapeutically effective amount of diquafosol or a salt thereof and does not comprise benzalkonium chloride to an eye wearing soft contact lens.

(20) A method of treating eye dryness or eye discomfort caused by wearing soft contact lens, which comprises administering an ophthalmic solution which comprises a therapeutically effective amount of diquafosol or a salt thereof and does not comprise benzalkonium chloride to an eye wearing soft contact lens.

Furthermore, the present invention relates to the following.

(21) An ophthalmic solution for treating dry eye, characterized by being applied to an eye of a dry eye patient wearing soft contact lens, which comprises diquafosol or a salt thereof as an active ingredient and does not comprise benzalkonium chloride.

(22) An ophthalmic solution for improving tear film stability, characterized by being applied to an eye wearing soft contact lens, which comprises diquafosol or a salt thereof as an active ingredient and does not comprise benzalkonium chloride.

(23) An ophthalmic solution for treating eye dryness or eye discomfort caused by wearing soft contact lens, characterized by being applied to an eye wearing soft contact lens, which comprises diquafosol or a salt thereof as an active ingredient and does not comprise benzalkonium chloride.

Effects of the Invention

The therapeutic agent for dry eye comprising diquafosol tetrasodium salt and not containing benzalkonium chloride treats onset and/or exacerbation of dry eye symptoms caused by wearing soft contact lens.

DESCRIPTION OF THE EMBODIMENTS

Figure 1:
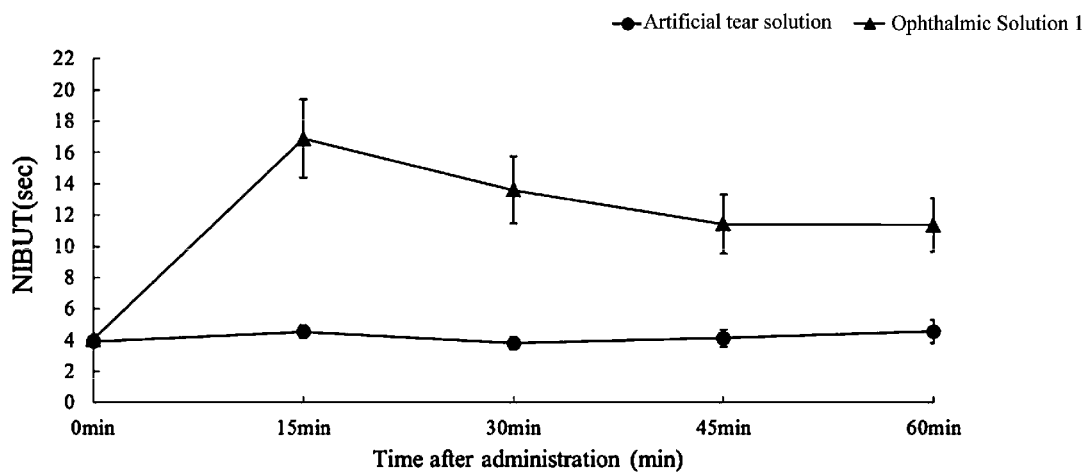
FIG. 1 is a graph showing the results of an Evaluation Test of NIBUT increasing effect in pharmacological test 1.

Diquafosol is a compound represented by the following formula.

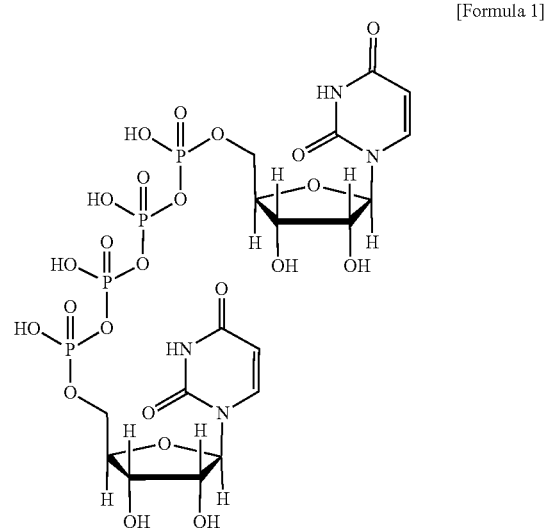

[Formula 1]

Diquafosol can be produced according to the usual method in the field of organic synthetic chemistry and can be also produced by the method disclosed in JP 2001-510484A.

There are no particular limitations on the diquafosol salt provided it is a salt that is acceptable for use as a pharmaceutical, and examples thereof include salts of an inorganic acid such as hydrochloric acid, hydrobromic acid, hydroiodic acid, nitric acid, sulfuric acid or phosphoric acid; salts of an organic acid such as acetic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate ester, methyl sulfate, naphthalenesulfonic acid or sulfosalicylic acid; quaternary ammonium salts of methyl bromide or methyl iodide; salts of a halogen ion such as bromine ion, chlorine ion or iodine ion; salts of an alkali metal such as lithium, sodium and potassium; salts of an alkaline earth metal such as calcium and magnesium; metal salts of iron or zinc; salts of ammonia; and salts of an organic amine such as triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine and N,N-bis(phenylmethyl)-1,2-ethanediamine.

As the "diquafosol or a salt thereof" in the present invention, preferred is a tetrasodium salt of diquafosol (hereinafter also simply referred to as "diquafosol sodium") represented by the following formula.

[Formula 2]

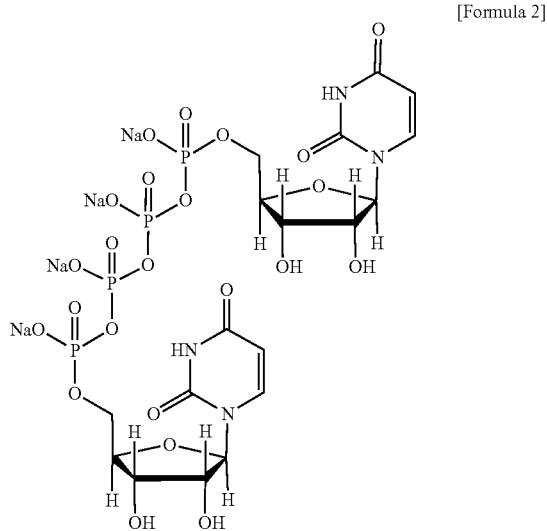

In the case diquafosol or a salt thereof has geometric isomers or optical isomers, these isomers or a salt thereof are also included in the scope of the present invention. In addition, in the case diquafosol or a salt thereof has proton tautomerism, these tautomers or a salt thereof are also included in the scope of the present invention.

In the case diquafosol or a salt thereof, a hydrate or a solvate has crystal polymorphism and crystal polymorphic groups (crystal polymorphic systems), these crystal polymorphs and crystal polymorphic groups (crystal polymorphic systems) are also included in the scope of the present invention. Here, a crystal polymorphic group (crystal polymorphic system) refers to individual crystalline forms at each stage in the case of undergoing a change in crystalline form according to conditions and state (incidentally, this state also includes formulated state), such as with respect to crystal production, crystallization, or storage and the like, as well as the entire process thereof.

Benzalkonium chloride is a preservative generally used in the ophthalmic solution, and represented by the formula: $[C_6H_5CH_2N(CH_3)_2R]Cl$. In the above-mentioned formula, R represents an alkyl group, benzalkonium chloride having the alkyl group of a carbon number of 12 (hereinafter also simply referred to as "BAK-$C_{12}$") or benzalkonium chloride having the alkyl group of a carbon number of 14 (hereinafter also simply referred to as "BAK-$C_{14}$") is, in particular, generally used in the ophthalmic solution.

In the present invention, "being applied to an eye of a dry eye patient wearing soft contact lens" means that an ophthalmic solution is applied onto cornea of a dry eye patient while soft contact lens is being worn.

Examples of soft contact lenses include contact lenses having hydroxyethyl methacrylate for the main component thereof, silicone hydrogel contact lenses and the like.

There are no particular limitations on the type of soft contact lens targeted for application of the present invention, and may be ionic or nonionic or hydrous or non-hydrous soft contact lenses. For example, the present ophthalmic solution can be applied to all other soft contact lenses currently available on the market or soft contact lenses to be available on the market in the future such as repeatedly usable contact lenses, one-day disposable contact lenses, one-week disposable contact lenses, two-week disposable contact lenses and the like.

Dry eye is defined as "a chronic disease of the tears and keratoconjunctival epithelium caused by various factors that is associated with eye discomfort and vision disorders", and keratoconjunctivitis sicca (KCS) is included in dry eye. In the present invention, the onset of symptoms of dry eye caused by wearing soft contact lenses is included in dry eye.

Symptoms of dry eye include subjective symptoms such as eye dryness, eye discomfort, eye fatigue, heavy eyes, photophobia, eye pain or blurred vision (bleariness), as well as objective symptoms such as hyperemia or keratoconjunctival epithelial disorders.

Although there are many aspects of the cause of dry eye that are unclear, reported examples of causes thereof include Sjogren's syndrome; congenital alacrima; sarcoidosis; graft versus host disease (GVHD) associated with bone marrow transplantation; ocular pemphigoid; Stevens-Johnson syndrome; lacrimal duct obstruction caused by trachoma or the like; diabetes; the decrease in reflex tear secretion caused by corneal refractive surgery (laser (-assisted) in situ keratomileusis (LASIK)) or the like; Meibomian gland dysfunction; oily layer reduction caused by blepharitis or the like; incomplete winking or incomplete eyelid closure caused by exophthalmos, lagophthalmos or the like; the decrease in the secretion of mucin from an goblet cell; visual display terminal (VDT) work, and so on.

In the present invention, the "treatment of dry eye" means the amelioration of dry eye symptoms by improving tear film stability in an eye wearing a soft contact lens. Incidentally, the amelioration of dry eye symptoms refers to the amelioration of dry eye symptoms derived from exacerbation resulting from the wearing of soft contact lenses by a patient with dry eye, and the amelioration of dry eye symptoms derived from the wearing of soft contact lenses per se. In addition, in the present invention, in the "treatment of dry eye" includes "prevention of dry eye".

Improvement of tear film stability refers to quantitative or qualitative improvement of lacrimal fluid. Furthermore, tear film stability can be confirmed by measuring tear break up time (BUT). BUT measured in a more natural state without applying a load in the form of a dye solution and the like is referred to as non-invasive tear break up time (NIBUT).

In the present invention, the "multi-dose type container" means an eye drop container having a container body and a cap attachable to the container body, and an eye drop container capable of freely subjecting to opening and resealing of the cap. In the multi-dose type container, an ophthalmic solution for multiple times is usually contained for a certain period of use.

In the present invention, the "unit-dose type container" means an eye drop container in which a cap is fusion sealed to a bottle mouth portion, which is intended to be used by breaking and opening the fusion bonded portion between the cap and the bottle shaped main body at the time of use. In the unit-dose type container, an ophthalmic solution for once or multiple times of uses is contained. In addition, in the unit-dose type container, it is also included a container in which a cap is fusion sealed to a bottle mouth portion, and after opening the container by breaking the fusion bonded portion between the cap and the bottle shaped main body at the time of use, complete capping is possible again, and which is an eye drop container containing an ophthalmic solution for several times of use to be used within a day.

In addition, to the present agent may be added a preservative other than benzalkonium chloride, and it may be a usual multi-dose type.

In the present invention, there are no particular limitations on the "preservative other than benzalkonium chloride" provided it is a compound other than benzalkonium chloride, and has been known to have a preservative effect, and preferably chlorhexidines, borates, chlorites, parabenes, sorbates, chlorobutanol and benzethonium chloride, further preferably chlorhexidines.

In the case the present agent contains chlorhexidines, the "chlorhexidines" include chlorhexidine and a salt thereof. Chlorhexidine is a compound represented by the following chemical structural formula, and is a compound also called as 1,1'-hexamethylenebis [5-(4-chlorophenyl) biguanide].

lates and/or inorganic acid salts are more preferable, gluconates, acetates and/or hydrochlorides are even more preferable, and gluconates are particularly preferable. One type of these chlorhexidine salts may be used alone or two or more types may be arbitrarily combined and used.

Chlorhexidine and a salt thereof may be synthesized by the conventionally known method or may be obtained as a commercially available product.

In the case the present agent contains chlorhexidines, the concentration is 0.0001 to 0.1%, preferably 0.0005 to 0.05% (w/v), and particularly preferably 0.001 to 0.005% (w/v).

In the case the present agent contains borates, the "borates" include boric acid and a salt thereof. Among the above-mentioned borates, there are no particular limitations on the "salt of boric acid" provided it is a salt that is acceptable for use as a pharmaceutical, and specific examples thereof include sodium borate, potassium tetraborate, potassium metaborate, ammonium borate, borax or the like, preferably borax.

In the case the present agent contains chlorites, the "chlorites" include chlorous acid and a salt thereof. Among the above-mentioned chlorites, there are no particular limitations on the "salt of chlorous acid" provided it is a salt that is acceptable for use as a pharmaceutical, and specific examples thereof include sodium chlorite, potassium chlorite, calcium chlorite, magnesium chlorite or the like.

In the case the present agent contains parabens, the "parabens" include paraben and a salt thereof. Among the above-mentioned parabens, there are no particular limitations on the "salt of paraben" provided it is a salt that is acceptable for use as a pharmaceutical, and specific examples thereof include ethyl paraoxybenzoate, methyl paraoxybenzoate, propyl paraoxybenzoate, isopropyl paraoxybenzoate, butyl paraoxybenzoate, isobutyl paraoxybenzoate or the like, preferably methyl paraoxybenzoate and ethyl paraoxybenzoate.

[Formula 3]

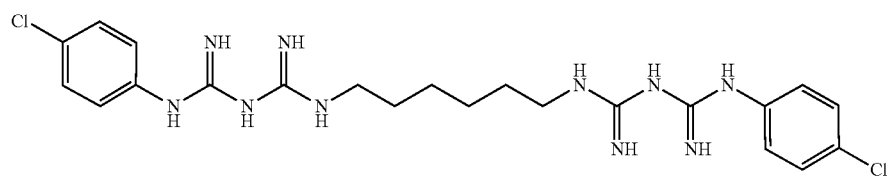

Among the aforementioned chlorhexidines, there are no particular limitations on the "chlorhexidine salt" provided it is a salt that is acceptable for use as a pharmaceutical, and specific examples thereof include organic acid salts [such as monocarboxylates (such as acetates, trifluoroacetates, butyrates, palmitates or stearates), polycarboxylates (such as fumarates, maleates, succinates or malonates), oxycarboxylates (such as gluconates, lactates, tartrates or citrates), and organic sulfonates (such as methanesulfonates, toluenesulfonates or tosylates)], inorganic acid salts (such as hydrochlorides, sulfates, nitrates, hydrobromides or phosphates), salts of organic bases (such as salts of organic amines such as methylamine, triethylamine, triethanolamine, morpholine, piperazine, pyrrolidone, tripyridine or picoline), and salts of inorganic bases [such as ammonium salts, alkali metals (such as sodium or potassium), alkaline earth metals (such as calcium or magnesium) or metals such as aluminum]. Among these salts, organic acid salts and/or inorganic acid salts are preferable, oxycarboxylates, monocarboxy- In the case the present agent contains sorbates, the "sorbates" include sorbic acid and a salt thereof. Among the above-mentioned sorbates, there are no particular limitations on the "salt of sorbic acid" provided it is a salt that is acceptable for use as a pharmaceutical, and specific examples thereof include potassium sorbate or the like.

A dosage form of the present agent is an ophthalmic solution.

The present agent may contain an active ingredient(s) other than the diquafosol or a salt thereof, and preferably contains the diquafosol or a salt thereof alone as a sole active ingredient.

The present agent contains diquafosol or a salt thereof in a concentration of preferably 0.5 to 5% (w/v), more preferably 1, 2, 3 or 4% (w/v), and further preferably 3% (w/v).

The present agent can be prepared by using materials selected from isotonicity agents such as sodium chloride, potassium chloride, concentrated glycerin or the like; buffers such as sodium phosphate, sodium acetate, ε-aminocaproic acid or the like; surfactants such as polyoxyethylene sorbitan monooleate, polyoxyl 40 stearate, polyoxyethylene hydrogenated castor oil or the like; stabilizers such as sodium citrate, disodium edetate or the like, and a pH may be within the allowable range for ophthalmic preparations, and is usually preferably within the range of 4 to 8. To the present agent may be optionally added pH adjusters such as hydrochloric acid or sodium hydroxide or the like.

The present agent may be applied to eyes with 1 to 10 times a day, preferably 2 to 8 times a day, more preferably 4 to 6 times a day, and further preferably 6 times a day.

In the following, the results of the pharmacological test and preparation example are shown, but these examples are for better understanding of the present invention and do not limit the scope of the present invention.

EXAMPLES

[Pharmacological Test 1] Evaluation Test of NIBUT Increasing Effect

The NIBUT values of a diquafosol ophthalmic solution were examined in eyes in which tear film stability had decreased as a result of wearing soft contact lenses.
(Sample Preparation)
Ophthalmic Solution 1 was prepared as a diquafosol ophthalmic solution and used in the test.
Ophthalmic Solution 1:
Diquafosol sodium (3 g), sodium hydrogen phosphate hydrate (0.2 g), sodium chloride (0.39 g), potassium chloride (0.15 g), disodium edetate hydrate (0.01 g) and chlorhexidine gluconate (0.0025 g) were dissolved in water and brought to a final volume of 100 mL, followed by the addition of a pH adjuster to adjust the pH to 7.5.
(Test Method)
NIBUT values before and at 15, 30, 45 and 60 minutes after applying Ophthalmic Solution 1 (20 μl/eye) were measured for the eyes wearing soft contact lenses of cynomolgus monkeys (product name: Menicon Soft MA®) with a dry eye observation system (DR-1, Kowa Co., Ltd.). An artificial tear solution (product name: Soft Santear®) was used as a control (N=10 to 11 eyes).
(Results)
The test results are shown in FIG. 1. As is clear from FIG. 1, when Ophthalmic Solution 1 was applied to the eyes wearing soft contact lenses, significant increases in NIBUT were observed in comparison with prior to application at all measurement points up to 60 minutes after application. On the other hand, increases in NIBUT were not observed in eyes applied with the artificial tear solution.
(Discussion)
On the basis of the above results, the present agent was shown to improve decreases in tear film stability caused by wearing soft contact lenses. Accordingly, the present agent is useful for treating onset and/or exacerbation of dry eye symptom caused by wearing soft contact lenses. That is, the present agent can treat dry eye by being applied to eyes wearing soft contact lens of a dry eye patient. In addition, it has been reported that wearing soft contact lenses causes a subjective symptom such as eye dryness or eye discomfort. This is considered to be caused by the fact that wearing soft contact lenses causes thinning of the tear film, whereby stability of the tear film is decreased. From the above-mentioned results, the present agent improves decreases in tear film stability caused by wearing soft contact lenses, so that it is useful for treating eye dryness or eye discomfort caused by wearing soft contact lenses.

[Pharmacological Test 2] Evaluation Test 2 of NIBUT Increasing Effect

Figure 2:
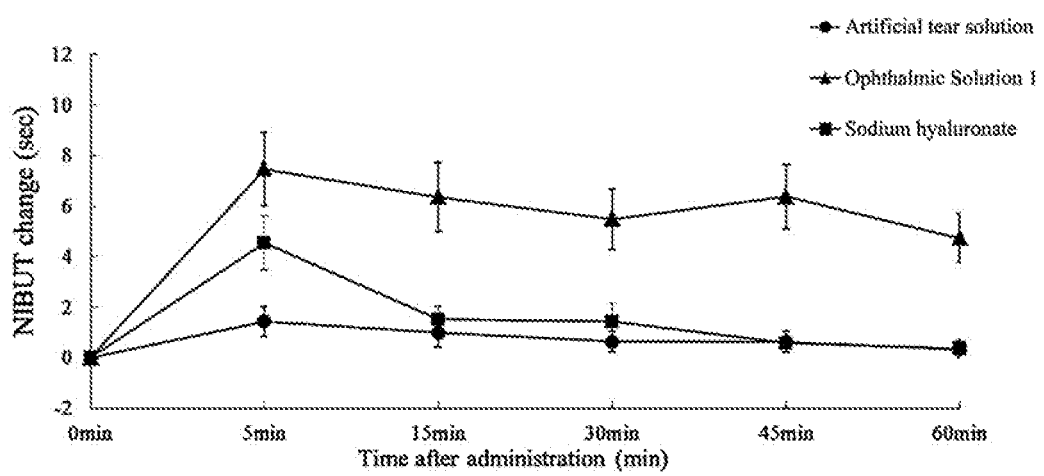
FIG. 2 is a graph showing the results of an Evaluation Test 2 of NIBUT increasing effect in pharmacological test 2.

The NIBUT values of a diquafosol ophthalmic solution were examined in eyes in which tear film stability had decreased as a result of wearing soft contact lenses.
(Sample Preparation)
Ophthalmic Solution 1 was prepared in the same manner as pharmacological test 1 as a diquafosol ophthalmic solution and applied to the test.
(Test Method)
NIBUT values before and at 5, 15, 30, 45 and 60 minutes after applying Ophthalmic Solution 1 (20 μl/eye) were measured for the eyes of cynomolgus monkeys wearing soft contact lenses (product name: Menicon Soft MA®) with a dry eye observation system (DR-1, Kowa Co., Ltd.). An artificial tear solution (product name: Soft Santear®) and sodium hyaluronate (product name: Hyalein® Mini Ophthalmic Solution 0.1%) was used as a control (N=11 eyes).
(Results)
The test results are shown in FIG. 2. As is clear from FIG. 2, when Ophthalmic Solution 1 was applied to the eyes wearing soft contact lenses, significant increases in NIBUT were observed in comparison with prior to application at all measurement points up to 60 minutes after application. On the other hand, increases in NIBUT were not observed in eyes applied with the artificial tear solution. In addition, although an increase in NIBUT was observed at 5 minutes after application in eyes applied with sodium hyaluronate, the increasing effect thereof was lower than that of Ophthalmic Solution 1 and increases in NIBUT were not observed at 15 minutes after application and beyond.
(Discussion)
On the basis of the above results, the present agent was shown to improve decreases in tear film stability caused by wearing soft contact lenses. The test results show that in the case of being applied to an eye wearing soft contact lens of a dry eye patient, the present agent exhibits an extremely strong effect for treating dry eye, an effect for treating eye dryness or eye discomfort caused by wearing soft contact lens more than Hyalein® Mini Ophthalmic Solution.

[Pharmacological Test 3] Comparative Test of NIBUT Increasing Effect

A comparative study of NIBUT values was conducted between the present ophthalmic solution and an ophthalmic solution containing benzalkonium chloride in eyes in which tear film stability had decreased as a result of wearing soft contact lenses.
(Sample Preparations)
Ophthalmic Solution 1:
Ophthalmic Solution 1 was prepared as the present ophthalmic solution in the same manner as in Pharmacological test.
Ophthalmic Solution 2:
Ophthalmic Solution 2 in which no preservative is contained was prepared as the present ophthalmic Solution. More specifically, diquafosol sodium (3 g), sodium hydrogen phosphate hydrate (0.2 g), sodium chloride (0.41 g), potassium chloride (0.15 g) and disodium edetate hydrate (0.01 g) were dissolved in water and brought to a final volume of 100 mL, followed by the addition of a pH adjuster to adjust the pH to 7.5.
Ophthalmic Solution 3:
Ophthalmic Solution 3 containing benzalkonium chloride was prepared for use as a comparative example. More specifically, diquafosol sodium (3 g), sodium hydrogen phosphate hydrate (0.2 g), sodium chloride (0.41 g), potassium chloride (0.15 g) and benzalkonium chloride (0.0075 g) were dissolved in water and brought to a final volume of 100 mL followed by the addition of a pH adjuster to adjust the pH to 7.5. Ophthalmic Solutions 1, 2 and 3 are ophthalmic solutions that comprise the same concentrations of active ingredient (diquafosol sodium). In addition, both Ophthalmic Solution 1 and Ophthalmic Solution 3 are ophthalmic solutions that comply with the preservative effectiveness test standards of the Japanese Pharmacopoeia and have equivalent preservative effectiveness.

(Test Method)

NIBUT values before and at 30 minutes after applying Ophthalmic Solutions 1 to 3 (20 μl/eye) were measured for the eyes of cynomolgus monkeys wearing soft contact lenses (product name: Menicon Soft MA®) with a dry eye observation system (DR-1, Kowa Co., Ltd.) (N=11 eyes).

(Results)

The test results are shown in Table 1.

TABLE 1

|  | Ophthalmic Solution 1 | Ophthalmic Solution 2 | Ophthalmic Solution 3 |
|---|---|---|---|
| NIBUT (sec) before application | 3.40 | 3.23 | 3.39 |
| NIBUT (sec) after application | 8.20 | 8.67 | 6.25 |

As a result of measuring and comparing NIBUT values at 30 minutes after applying Ophthalmic Solution 1 or Ophthalmic Solution 3, which comply with the preservative effectiveness test standards of the Japanese Pharmacopoeia and have equivalent preservative effectiveness, Ophthalmic solution 1 was shown to have higher NIBUT increasing effect than Ophthalmic solution 3 containing benzalkonium chloride. In addition, the ophthalmic solution containing no preservative (Ophthalmic solution 2) was also shown to have higher NIBUT increasing effect than Ophthalmic solution 3 containing benzalkonium chloride.

(Discussion)

Based on the above results, the present ophthalmic solution was shown to improve decreases in tear film stability caused by wearing soft contact lenses more than an ophthalmic solution comprising benzalkonium chloride.

Preparation Example

Although the following provides a more detailed explanation of preparations of the present invention by indicating examples thereof, the present invention is not limited to these Preparation Examples.

Preparation Example 1: Ophthalmic Solution (3% (w/v))

| In 100 ml | |
|---|---|
| Diguasofol sodium | 3 g |
| Sodium hydrogen phosphate hydrate | 0.1-0.5 g |
| Sodium chloride | 0.01-1 g |
| Potassium chloride | 0.01-1 g |
| Disodium edetate hydrate | 0.0001-0.1 g |
| Chlorhexidine gluconate | 0.0001-0.1 g |
| Polysorbate 80 | 0.0001-0.1 g |
| Sterile purified water | q.s. |

Diquafosol sodium and other ingredients listed above are added to sterile purified water and they are mixed sufficiently so that this ophthalmic solution can be prepared.

INDUSTRIAL APPLICABILITY

The ophthalmic solution containing diquafosol tetrasodium salt and not containing benzalkonium chloride treats onset and/or exacerbation of dry eye symptoms by wearing soft contact lenses.

The invention claimed is:

1. A method of ameliorating eye dryness or eye discomfort caused by wearing soft contact lens comprising administering an ophthalmic solution which comprises a therapeutically effective amount of diquafosol or a salt thereof alone as a sole active ingredient and does not comprise benzalkonium chloride to an eye wearing soft contact lens, wherein a concentration of the diquafosol or a salt thereof is 3% (w/v) and the solution comprises a buffer, an isotonicity agent, a stabilizer and a pH adjuster.

2. The method according to claim 1, wherein the ophthalmic solution does not comprise a preservative.

3. The method according to claim 1, wherein the ophthalmic solution is contained in a unit-dose type container.

4. The method according to claim 1, wherein the ophthalmic solution is contained in a multi-dose type container.

* * * * *